(12) United States Patent
Caine et al.

(10) Patent No.: US 7,846,973 B2
(45) Date of Patent: Dec. 7, 2010

(54) CHEMICAL PROCESS AND NEW CRYSTALLINE FORM

(75) Inventors: Darren Michael Caine, Stevenage (GB); Ian Leonard Paternoster, Stevenage (GB); Peter David Penberthy Shapland, Stevenage (GB)

(73) Assignee: Theravance, Inc., South San Francisco, CA (US)

(*) Notice: Subject to any disclaimer, the term of this patent is extended or adjusted under 35 U.S.C. 154(b) by 711 days.

(21) Appl. No.: 10/599,145

(22) PCT Filed: Mar. 30, 2005

(86) PCT No.: PCT/GB2005/001241

§ 371 (c)(1), (2), (4) Date: Oct. 26, 2007

(87) PCT Pub. No.: WO2005/095328

PCT Pub. Date: Oct. 13, 2005

(65) Prior Publication Data

US 2010/0063157 A1    Mar. 11, 2010

Related U.S. Application Data

(60) Provisional application No. 60/574,467, filed on May 26, 2004.

(30) Foreign Application Priority Data

Apr. 2, 2004  (GB) ................................. 0407521.4
May 25, 2004  (GB) ................................. 0411688.5

(51) Int. Cl.
    *A61K 31/135*   (2006.01)
(52) U.S. Cl. ..................................... 514/653
(58) Field of Classification Search ................. 514/653
    See application file for complete search history.

(56) References Cited

U.S. PATENT DOCUMENTS

| | | | |
|---|---|---|---|
| 4,353,656 A | 10/1982 | Sohl et al. |
| 4,778,054 A | 10/1988 | Newell et al. |
| 4,811,731 A | 3/1989 | Newell et al. |
| 5,495,054 A | 2/1996 | Gao et al. |
| 5,552,438 A | 9/1996 | Christensen, IV |
| 5,590,645 A | 1/1997 | Davies et al. |
| 5,860,419 A | 1/1999 | Davies et al. |
| 5,873,360 A | 2/1999 | Davies et al. |
| 6,268,533 B1 | 7/2001 | Gao et al. |
| 6,321,747 B1 | 11/2001 | Dmitrovic et al. |
| 6,576,793 B1 | 6/2003 | Moran et al. |
| 6,632,666 B2 | 10/2003 | Baust et al. |

FOREIGN PATENT DOCUMENTS

| | | |
|---|---|---|
| EP | 069715 | 1/1983 |
| GB | 2064336 | 6/1981 |
| GB | 2129691 | 5/1984 |
| GB | 2169265 | 7/1986 |
| GB | 2178965 | 2/1987 |
| GB | 2242134 | 9/1991 |
| WO | 01/42193 | 6/2001 |
| WO | 03/042164 | 5/2003 |
| WO | 03/061743 | 7/2003 |
| WO | 2004/011416 | 2/2004 |
| WO | 2004/024728 | 3/2004 |
| WO | 2004/106279 | 12/2004 |

OTHER PUBLICATIONS

Caira, "Crystalline polymorphism of organic compounds," *Topics in Current Chemistry* 198:163-208 (1998).
Gould, "Salt Selection for basic Drugs," *International Journal of Pharmaceutics* 33(1/3):201-217 (1986).
Hett et al., Large-scale synthesis of enantio- and diastereomerically pure (R,R)-formoterol, *Organic Process Research & Development* 2(2):96-99 (Mar. 1998).
Hong et al., "cis-1-amino-2-indanol in asymmetric synthesis. Part 1. A practical catalyst system for the enantioselective borane reduction of aromatic ketones," *Tetrahedron Letters* 35(36):6631-6634 (Sep. 1994).

*Primary Examiner*—Raymond J Henley, III
(74) *Attorney, Agent, or Firm*—Jeffrey A. Hagenah; Roberta P. Saxon (57) ABSTRACT

The present invention relates to the preparation of a $\beta_2$ adrenergic agonist in crystalline salt form. In particular the invention relates to preparation of a crystalline salt of compound (I)

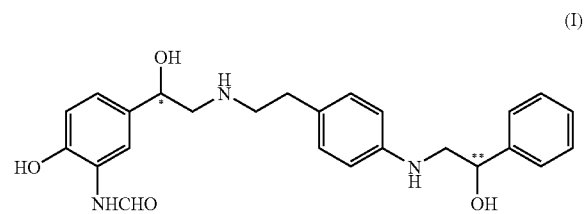

(I)

in particular a crystalline monohydrochloride salt. The invention also relates to a new crystalline form (polymorph) of the monohydrochloride salt of compound (Ia) and a process for preparing it.

24 Claims, 3 Drawing Sheets

CHEMICAL PROCESS AND NEW CRYSTALLINE FORM

CROSS-REFERENCE TO RELATED APPLICATIONS

This application is filed pursuant to 35 U.S.C. §371 as a United States National Phase Application of International Application No. PCT/GB2005/001241 filed 30 Mar. 2005, which claims priority from Great Britain Application Nos. 0407521.4 and 0411688.5 filed 2 Apr. 2004 and 25 May 2004 respectively, and U.S. Provisional Application No. 60/574,467 filed 26 May 2004.

FIELD OF THE INVENTION

The present invention relates to the preparation of a $\beta_2$ adrenergic agonist in crystalline salt form. In particular the invention relates to preparation of a crystalline salt of compound (I) defined below. More particularly the invention relates to a process for preparing a crystalline monohydrochloride salt of compound (Ia) defined below. The invention also relates to a new crystalline form (polymorph) of the monohydrochloride salt of compound (Ia).

BACKGROUND OF THE INVENTION $\beta_2$ Adrenergic receptor agonists are recognized as effective drugs for the treatment of pulmonary diseases such as asthma and chronic obstructive pulmonary disease (including chronic bronchitis and emphysema). $\beta_2$ Adrenergic receptor agonists are also recognised as useful for treating premature labour, and are potentially useful for treating neurological disorders and cardiac disorders.

International Patent Application WO 01/42193 and corresponding U.S. Pat. No. 6,576,793 disclose inter alia a novel compound of the formula (I):

(I)

wherein the stereochemistry at *C and **C may be inter alia (R) and (R). This compound may be more particularly represented by the formula (Ia):

(Ia)

Compound (Ia) may variously be referred to by the chemical names N-{2-[4-((R)-2-hydroxy-2-phenylethylamino) phenyl]ethyl}-(R)-2-hydroxy-2-(3-formamido-4-hydroxyphenyl)ethylamine; N-[3-[(1R)-1-hydroxy-2-[[2-[4-[((2R)-2-hydroxy-2-phenylethyl)amino]phenyl]ethyl]amino]ethyl-6-hydroxyphenyl]-formamide and (α-R)-3-formamido-4-hydroxy-(α-[[[p-(N-((2R)-hydroxy-phenethyl))-aminophenethyl]amino]methyl benzyl alcohol. In CAS format the compound (Ia) is designated:

N-[2-hydroxy-5-[(1R)-1-hydroxy-2-[[2-4-[[(2R)-2-hydroxy-2-phenylethyl]amino]phenyl]ethyl]amino]ethyl] phenyl]-formamide.

WO 01/42193 and U.S. Pat. No. 6,576,793 disclose Compound (Ia) as a potent β2 adrenergic receptor agonist.

WO 01/42193 and U.S. Pat. No. 6,576,793 describe the preparation of compound (Ia) as a mixture of stereoisomers, that is, wherein the stereochemistry at *C is (RS) and the stereochemistry at **C is (RS), according to the following reaction scheme:

Scheme 1 wherein Bn represents a benzyl protecting group.

U.S. patent application Ser. No. 10/627,555 and corresponding International published application WO 04/011416 describe the crystalline dihydrochloride salt of compound (Ia) and methods for preparing said salt. In said applications, compound (Ia) is prepared according to the following reaction scheme 2:

Scheme 2

In Scheme 2 the abbreviations used have the following meanings:

NaHMDS: sodium hexamethyldisilazane

THF: tetrahydrofuran

DMPU: 1,3-dimethyl-3,4,5,6-tetrahydro-2(1H)pyrimidinone

TBDMSCl: tert-butyldimethylsilylchloride

DMF: dimethylformamide

DMSO: dimethylsulphoxide

TREAT HF: triethylamine trihydrofluoride

The numbering of compounds in Scheme 2 follows that in WO 04/011416, but it will be appreciated that compound 1 in Scheme 2 is equivalent to compound (Ia) herein.

According to WO 04/011416, the dihydrochloride salt of compound 1 is prepared by dissolving compound 1 in a polar solvent to form a first solution and adding hydrochloric acid to form a second solution from which the dihydrochloride salt is formed by crystallisation.

WO 2004/106279 (claiming priority from U.S. Patent Application Ser. No. 60/473,423) describes a crystalline form of N-{2-[4-((R)-2-hydroxy-2-phenylethylamino)phenyl]ethyl}-(R)-2-hydroxy-2-(3-formamido-4-hydroxyphenyl)ethylamine monohydrochloride.

WO 2004/106279 describes inter alia the following methods for preparing the crystalline monohydrochloride salt of compound 1:

i) the addition of between about 0.9 and about 1 molar equivalent of aqueous hydrochloric acid to the active compound 1 dissolved in a polar solvent, such as isopropanol or water;

ii) the addition of a molar excess of an aqueous solution of an inorganic chloride at a pH of between about 5 and about 6 to the active compound 1 dissolved in a polar, water soluble solvent. A suitable source of chloride ions is ammonium chloride and a suitable polar solvent is isopropanol. For example the crystalline monoHCl salt can be formed by dissolving compound 1 in isopropanol, adding aqueous ammonium chloride, and allowing the solution to stand overnight at room temperature. The crystalline product can be isolated by filtration and dried.

iii) from a water slurry of the corresponding dihydrochloride salt, which slurry may be formed by the addition of water is added to the diHCl salt of compound 1.

iv) recrystallizing a hydrochloride salt of compound 1 having between 1 and 2 equivalents of chlorine per mole of compound 1.

SUMMARY OF THE INVENTION

We have now found an improved method for preparing a monohydrochloride salt of compound (I), in particular a monohydrochloride salt of compound (Ia) and most preferably a crystalline monohydrochloride salt of compound (Ia).

It will be appreciated from the foregoing that the compound of formula (I) includes two asymmetric centres, namely at the carbon atoms designated in formula (I) as *C and **C. References herein to compounds of formula (I) include both (S) and (R) enantiomers either in substantially pure form or admixed in any proportions, at both *C and **C. Thus, the stereochemistry at *C and **C may be (RS) and (RS), (R) and (R), (R) and (S), (S) and (R), or (S) and (S).

Hereinafter references to compound (I) should be read as including in particular compound (Ia) unless otherwise specified.

Thus, in a first aspect the present invention provides a process (A) for preparing a monohydrochloride salt of compound (I) which process comprises the steps of:

Aa) contacting a protected form of compound (I), or compound (Ia) (hereinafter compound (II) and (IIa) respectively):

(II)

(IIa)

wherein $P^1$ represents a hydroxyl protecting group, and $P^2$ and $P^3$ each independently represent hydrogen or a hydroxyl protecting group;
with a weak acid, to effect selective protonation;

Ab) contacting the product of (a) with a source of chloride ions to effect anion exchange;

Ac) deprotecting the product of (b) to remove $P^1$, and where necessary $P^2$ and $P^3$;

Ad) isolation of compound (I) or (Ia) as a monohydrochloride salt; and optionally Ae) crystallisation or recrystallisation of compound (I) or (Ia).

DETAILED DESCRIPTION

In a preferred embodiment the invention provides said process for the preparation of a monohydrochloride salt of compound (Ia), in particular for preparation of a crystalline monohydrochloride of compound (Ia).

Hydroxyl protecting groups $P^1$, $P^2$ and $P^3$ may be selected from amongst the wide range of known protecting groups using principles well known in the art. Examples of the hydroxyl protecting group $P^1$ include arylalkyl eg. benzyl. Where either or both of $P^2$ and $P^3$ represent protecting groups these may be groups which can be selectively removed under conditions which do not also remove $P^1$. Thus, each of $P^2$ and $P^3$ may be for example a silyl group, eg. a trialkyl silyl group such as tert-butyldimethyl silyl. In one embodiment of this invention $P^1$ represents a protecting group and $P^2$ and $P^3$ both represent hydrogen. Whether to employ a protecting group and if so the choice of protecting group is within the remit of the skilled person and may be achieved without undue experimentation.

It will be appreciated by those skilled in the art that compounds (I) and (Ia) contain two basic nitrogen atoms and thus have the potential to from salts at both. In order to obtain a monohydrochloride directly, ie. by reaction of compound (II) or (IIa) with hydrochloric acid, the reaction must be carefully controlled to achieve the correct stoichiometry, and avoid formation of eg. a dihydrochloride salt.

We have found that effecting initial protonation with a weak acid such as acetic acid results in selective protonation of only one nitrogen atom (the more basic nitrogen atom) and, following anion exchange, formation of a stoichiometrically exact monohydrochloride salt. The process of the present invention also has the advantage that the hydrochloride salt can be prepared without the use of strong acid. It is desirable to avoid the use of a strong acid as this can lead to deformylation of the parent compound.

In step (Aa) of the present process, a compound of formula (II) or (IIa) may be contacted with a weak acid. Conveniently this step may be effected in an organic solvent, for example a ketone such as 2-butanone (methylethylketone) or diethylketone, or a water-immiscible alcohol such as 1-pentanol. Weak acids which may be employed include for example acetic acid, 2-methoxybenzoic acid or 4-methoxybenzoic acid, preferably acetic acid. The weak acid may for example have a pKa in the range 4-5. This step may conveniently be effected at a slightly elevated temperature, for example at a temperature in the range from about 25° C. to about 50° C.

Step (Ab) may conveniently be effected without isolating the product from step (Aa). Thus for example the solution obtained from step (Aa) may be contacted with a source of chloride ions, using eg. aqueous sodium chloride. This step may also conveniently be effected at a temperature in the range from about 25° C. to about 50° C. At this stage the intermediate product may be isolated using conventional methods to provide the monohydrochloride salt of compound (II) or (IIa). This product may be obtained in crystalline form. If necessary crystallisation may be facilitated by standard methods, such as stirring, cooling, scratching or seeding.

Deprotection of (II) or (IIa) according to step (Ac) may be effected by conventional methods. Thus where one or both of $P^2$ and $P^3$ represents a silyl group this may be removed for example using cesium fluoride, in an organic solvent such as methanol, optionally in admixture with a further solvent such as diethylketone, methylethylketone or n-butylacetate, or triethylamine trifluoride in a solvent such as tetrahydrofuran. A protecting group $P^1$ may be removed for example by hydrogenation using a palladium or platinum catalyst eg. Pd/C, conveniently in an organic solvent such as N-methylpyrrolidone.

Monohydrochloride salt of compound (I) or (Ia) prepared according to the present invention may be isolated by conventional means. Advantageously said monohydrochloride salt of compound (Ia) may be obtained in crystalline form, by precipitation from an aqueous organic solution. In a particular embodiment crystalline (Ia) monohydrochloride may be obtained from an organic solution comprising a mixture of N-methylpyrrolidone and isopropylalcohol (preferably 1:1), by heating said solution to a temperature in the range from about 60° C. to about 80° C., adding water and then contacting the resulting aqueous solution with further isopropyl alcohol. During addition of further isopropyl alcohol the temperature is cooled, initially in the range from about 15° C. to about 25° C. and subsequently in the range from about 0° to about 10°.

Recrystallisation of monohydrochloride salt of compound (Ia) may be effected by suspending or dissolving said compound in a suitable solvent, for example industrial methylated spirits or methanol, in admixture with water. The resulting suspension or solution may if necessary be heated for example to a temperature in the range from about 60° C. to about 80° C. Crystallisation may be initiated in conventional manner, eg. with cooling and/or seeding.

In initial experiments we found that crystalline compound (Ia) monohydrochloride was obtained not only in the same crystalline form as described and characterised in WO 2004/106279 (hereinafter Form 1), but also in a new crystalline form, referred to herein as Form 2. We further found that Form 2 crystals are a more thermodynamically stable form than the Form 1 crystals.

Moreover, we have found that a mixture of Form 1 and Form 2 crystals of compound (Ia) monohydrochloride can be converted to substantially pure Form 2 crystals by slurrying, for example by suspending a mixture of Form 1 and Form 2 crystals in a solvent such as aqueous industrial methylated spirit or methanol and stirring at a temperature in the range from about 10° C. to about 50° C., for an extended period, e.g. up to 10 days, or by a process involving recrystallisation with temperature cycling. Such methods can be used to provide seeds of Form 2 material.

Thus, in a particular embodiment of process A recrystallisation of the monohydrochloride salt obtained may be effected by subjecting a suspension of (Ia) monohydrochloride to repeated cycles of heating and cooling. Heating may be effected at a temperature in the range from about 50° C. to about 60° C. and cooling in the range from about 15° C. to 25° C. The solution or suspension may be aged after each phase of heating and/or cooling. The heating and cooling steps may be repeated for several cycles, for example 2-5 cycles.

Form 1 and Form 2 of the crystalline (Ia) monohydrochloride may be distinguished using Differential Scanning Calorimetry analysis, X-ray powder diffraction, and/or infra-red spectroscopy as described hereinafter. Form 2 crystalline (Ia) monohydrochloride has been found to be more thermodynamically stable than Form 1.

The present invention thus also provides crystalline (Ia) monohydrochloride (namely, crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride) in a form (Form 2) which is characterised by a differential scanning calorimetry trace which shows an absence of discernable endothermic features below about 125° C., two or more minor endothermic events between about 130° C. and about 180° C. and an onset of significant endothermic heat flow at about 229° C. For example, said minor endothermic events may occur at about 133° C. and at about 151° C.; in addition a further minor endothermic event may occur at about 170° C.

Form 2 crystalline (Ia) monohydrochloride may also be characterised by infra red spectroscopy. Thus, when the infra-red absorption spectrum was recorded over the wavenumber range 4000 to 650 cm$^{-1}$ using a PerkinElmer Spectrum One FT-IR spectrometer equipped with a PerkinElmer Universal ATR (attenuated total reflection) sampling accessory Form 2 crystalline (Ia) monohydrochloride gave an infrared absorption spectrum with significant absorption bands at about 663, 698, 747, 764, 788, 809, 827, 875, 969, 995, 1024, 1056, 1081, 1101, 1212, 1294, 1371, 1440, 1520, 1543, 1596, 1659, 3371 and 3552 cm$^{-1}$.

Form 2 crystalline (Ia) monohydrochloride may also be characterised by X-ray powder diffraction, for example as in FIGS. 1 and 2 hereinafter.

In a yet further embodiment the present invention provides Form 2 crystalline (Ia) monohydrochloride in substantially pure form. As used herein the term 'substantially pure' means crystalline (Ia) monohydrochloride wherein more than 50% by weight in Form 2, suitably at least 75% by weight is Form 2, for example, at least 80%, suitably at least 85%, preferably at least 90% by weight.

Form 2 crystalline (Ia) monohydrochloride may be obtained in substantially pure form by controlling the crystallisation or recrystallisation of the (Ia) monohydrochloride, for example in step (e) of the process of the present invention. In general it is desirable to effect the crystallisation with temperature cycling as described hereinabove.

Thus in a further aspect the present invention also provides a process (B) for obtaining Form 2 crystalline (Ia) monohydrochloride (as defined herein) which comprises:

Ba) Forming a mixture of N-{2-[4-(R)-2-hydroxy-2-phenylethylamino)phenyl]ethyl}-(R)-2-hydroxy-2-(3-formamido-4-hydroxyphenyl)ethylamine monohydrochloride in an aqueous organic solvent, by contacting said monohydrochloride with said solvent and heating in a range from about 60° C. to about 70° C., for example about 65° C.;

Bb) Adjusting the temperature of said mixture in the range from about 52° C. to about 58° C.; for example about 55° C.;

Bc) Seeding said mixture with Form 2 crystals;

Bd) cooling said mixture to a temperature in the range from about 15° C. to 25° C.;

Be) heating said mixture to a temperature in the range from about 47° C. to about 52° C., for example about 50° C.;

Bf) repeating steps Bd) and Be) to obtain the desired Form 2.

In step Ba) of the above process the aqueous organic solvent may be for example an aqueous alcohol such as aqueous methanol or aqueous industrial methylated spirits. On heating in the specified temperature range the mixture should form a solution in the organic solvent. If necessary or desired at this stage the solution may be clarified, eg by filtration to remove impurities.

In step Bc) the seeding may be effected with crystalline material prepared as described hereinbefore. After seeding a suspension forms. The mixture may be aged after each phase of heating and/or cooling. The period of aging may be for example from about 0.25 hour to about 3.00 hours. The heating and cooling steps Bd) and Be) may be repeated for several cycles, for example 2-5 cycles. Thus for example the solution or suspension of (Ia) monohydrochloride may be initially heated to a temperature in the range of about 60° C. to about 70° C., e.g. 65±2° C., cooled to a temperature in the range 50° C. to 60° C., e.g 55±2° C., seeded, aged for about 30 minutes, then cooled over a period of about 2 hours to about 20° C. In subsequent cycles the solution or suspension may be heated to about 50° C. and cooled to about 10° C.

The N-{2-[4-(R)-2-hydroxy-2-phenylethylamino)phenyl]ethyl}-(R)-2-hydroxy-2-(3-formamido-4-hydroxyphenyl)ethylamine monohydrochloride employed as a starting material for the preparation of Form 2 may be prepared for example by the method of process A above or as described in WO 04/011416.

The compound of formula (II) or (IIa) wherein $P^2$ and $P^3$ both represent hydrogen may be obtained from a corresponding compound of formula (III).

(III)

wherein $P^1$ and $P^3$ are as defined for compound (II) and $P^{2'}$ is a hydroxyl protecting group. $P^{2'}$ may be selected from hydroxyl protecting groups known in the art, e.g. a silyl group such as tert-butyldimethylsilyl. It will be appreciated that $P^1$, $P^{2'}$ and $P^3$ should be selected such that $P^{2'}$ and $P^3$ can be removed under conditions which will not also remove $P^1$.

When $P^{2'}$ represents a tert-butyldimethylsilyl group this may conveniently be removed using cesium fluoride, in an organic solvent such as methanol, optionally in admixture with a further solvent such as diethylketone, methylethylketone or n-butylacetate.

It will be understood that when it is desired to obtain a compound (Ia) the appropriate chiral intermediate is desirably employed in this stage and in the stages described hereinafter. Structures (III) (IV) and (V) should therefore be interpreted as depicting the individual chiral forms as well as mixtures thereof.

A compound (III) may be obtained by reaction of a compound (IV):

(IV)

wherein Hal is a halo leaving group, eg. bromo, and $P^{2'}$ is as defined for formula (III) with a compound (V):

(V)

or a salt thereof, eg a hydrobromide salt, wherein $P^3$ is as defined for formula (III).

The reaction of (IV) and (V) may conveniently be effected in the presence of a base, such as potassium carbonate and in a solvent such as N,N-dimethylacetamide or N-methylpyrrolidinone.

Compounds (IV) and (V) may be coupled, in a solvent such as N,N-dimethylacetamide or dimethylsulphoxide, by adding potassium carbonate and sodium hydroxide or sodium iodide and heating to a temperature in the range of about 90° C. to about 140° C. to form a compound (III), which may be further reacted without isolation.

The compound (V) may be obtained by coupling 2-(4-aminophenyl)ethylamine and styrene oxide.

It will be appreciated that to prepare a compound (Ia), the correct chiral form of compound (V) should be employed. This may be prepared by employing (R)-styrene oxide in the above reaction.

The amine, which is optionally provided as a salt, may first be reacted with between about 1 and about 1.2 equivalents of a base having a $pK_a$ value greater than about 18, in order to substantially deprotonate the 4-amino group and the (R)-styrene oxide added to the product of the amine reaction. Useful basic compounds include sodium bis(trimethylsilyl) amide, alternatively known as sodium hexamethyldisilazane (NaHMDS), lithium diisopropyl amide, and n-butyl lithium. The reaction is preferably conducted in a solvent system including a polar aprotic solvent, such as 1,3-dimethyl-3,4,5,6-tetrahydro-2(1H)pyrimidinone (DMPU). Additional examples of aprotic polar solvents include dimethylsulfoxide, N-methyl pyrrolidinone, N; N-dimethyl acetamide, tetramethylethylenediamine, and hexamethylphosphoramide. After aqueous extraction, the product of the coupling reaction may be crystallized as a salt, for example the hydrochloride or hydrobromide salt, from a solvent such as isopropanol, by the addition of aqueous hydrochloric or aqueous hydrobromic acid. The crystallization procedure efficiently separates the desired product from side products formed during the reaction. The hydrochloride salt may be redissolved with 10 N aqueous sodium hydroxide to provide 2-[4-((R)-2-hydroxy-2-phenylethylamino) phenyl]ethylamine (compound (V)). The hydrobromide salt however can be used directly in the next step.

The corresponding (S) stereoisomer, 2-[4-(S)-2-hydroxy-2-phenylethylamino)phenyl]ethylamine, can be prepared by substituting (S)-styrene oxide for (R)-styrene oxide in the above procedure for the synthesis of compound (V).

Compounds of formula (IV) may be prepared by methods known in the art. Thus for example a compound of formula (IV) wherein $P^2$ is hydrogen may be prepared as described in U.S. Pat. No. 6,268,533 B1; and in R. Hett et al., Organic Process Research and Development, 1998, 2, 96-99, or using procedures similar to those described by Hong et al., Tetrahedron Ltt., 1994, 35, 6631; or similar to those described in U.S. Pat. No. 5,495,054. A protecting group $P^2$ may be introduced by standard methods, for example by the addition of tert-butydimethylsilylchloride (TBDMS-Cl) and dissolved in a suitable solvent such as dichloromethane.

In a further aspect the present invention provides a method for the prophylaxis or treatment of a clinical condition in a mammal, such as a human, for which a $\beta_2$-adrenoreceptor agonist is indicated, which comprises administration of a therapeutically effective amount of Form 2 crystalline (Ia) monohydrochloride. In particular, the present invention provides such a method for the prophylaxis or treatment of a disease associated with reversible airways obstruction such as asthma, chronic obstructive pulmonary disease (COPD), respiratory tract infection or upper respiratory tract disease.

In the alternative, there is also provided a Form 2 crystalline (Ia) monohydrochloride for use in medical therapy, particularly, for use in the prophylaxis or treatment of a clinical condition in a mammal, such as a human, for which a $\beta_2$-adrenoreceptor agonist is indicated. In particular, there is provided Form 2 crystalline (Ia) monohydrochloride for the prophylaxis or treatment of a disease associated with reversible airways obstruction such as asthma, chronic obstructive pulmonary disease (COPD), respiratory tract infection or upper respiratory tract disease.

The present invention also provides the use of Form 2 crystalline (Ia) monohydrochloride in the manufacture of a medicament for the prophylaxis or treatment of a clinical condition for which a $\beta_2$-adrenoreceptor agonist is indicated, for example a disease associated with reversible airways obstruction such as asthma, chronic obstructive pulmonary disease (COPD), respiratory tract infection or upper respiratory tract disease.

The amount of Form 2 crystalline (Ia) monohydrochloride which is required to achieve a therapeutic effect will, of course, vary with the route of administration, the subject under treatment, and the particular disorder or disease being treated. The compound of the invention may be administered by inhalation at a dose of from 0.0005 mg to 1 mg, preferably 0.001 mg to 0.1 mg. eg. 0.005 mg to 0.05 mg. The dose range for adult humans is generally from 0.0005 mg to 0.5 mg per day, e.g. from 0.0005 to 0.1 mg per day, conveniently 0.001 mg to 0.05 mg per day, e.g. 0.005 mg to 0.05 mg.

While it is possible for Form 2 crystalline (Ia) monohydrochloride to be administered alone, it is preferable to present it as a pharmaceutical formulation.

Accordingly, the present invention further provides a pharmaceutical formulation comprising Form 2 crystalline (Ia) monohydrochloride and a pharmaceutically acceptable carrier or excipient, and optionally one or more other therapeutic ingredients.

Hereinafter, the term "active ingredient" means Form 2 crystalline (Ia) monohydrochloride or a form of compound (Ia) derived from said crystalline form.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (eg. lactose or starch). Use of lactose is preferred. Powder blend formulations may also contain a ternary agent such as a sugar ester, for example cellobiose octaacetate, or a stearate such as magnesium stearate or calcium stearate.

Each capsule or cartridge may generally contain between 20 μg-10 mg of the active ingredient optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134, U.S. Pat. Nos. 6,632,666, 5,860,419, 5,873, 360 and 5,590,645 or Diskhaler, see GB 2178965, 2129691 and 2169265, U.S. Pat. Nos. 4,778,054, 4,811,731, 5,035, 237) or metered in use (eg as in Turbuhaler, see EP 69715 or in the devices described in U.S. Pat. No. 6,321,747). An example of a unit-dose device is Rotahaler (see GB 2064336 and U.S. Pat. No. 4,353,656). The Diskus inhalation device comprises an elongate strip formed from a base sheet having a plurality of recesses spaced along its length and a lid sheet hermetically but peelably sealed thereto to define a plurality of containers, each container having therein an inhalable formulation containing active ingredient preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet. Alternatively, the formulation may be presented if desired together with one or more other therapeutic agents in an inhalation device wherein the individual therapeutic agents are administrable simultaneously but are stored separately (or wholly or partly stored separately for triple combinations), e.g. in separate pharmaceutical compositions, for example as described in WO 03/061743.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the active ingredient optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compound and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising Form 2 crystalline (Ia) monohydrochloride together with one or more other therapeutically active agents, for example selected from an anti-inflammatory agent (for example a corticosteroid or an NSAID), an anticholinergic agent, another 32-adrenoreceptor agonist, an antiinfective agent (e.g. an antibiotic or an antiviral), or an antihistamine. Preferred are combinations comprising Form 2 crystalline (Ia) monohydrochloride together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Anti-inflammatory agents include corticosteroids. Preferred corticosteroids include fluticasone propionate, $6\alpha,9\alpha$-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and $6\alpha,9\alpha$-difluoro-17α-[(2-furanylcarbonyl)oxy]-11β-hydroxy-16α-methyl-3-oxo-androsta-1,4-diene-17β-carbothioic acid S-fluoromethyl ester, more preferably $6\alpha,9\alpha$-difluoro-17α-[2-furanylcarbonyl)oxy]-11β-hydroxy-16α-methyl-3-oxo-androsta-1,4-diene-17β-carbothioic acid S-fluoromethyl ester.

Anti-inflammatory agents also include non-steroidal anti-inflammatory drugs (NSAID's). NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors.

A PDE4-specific inhibitor may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds of interest include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Another compound of interest is cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438. Further compounds of interest are disclosed in the published international patent application WO04/024728 (Glaxo Group Ltd), PCT/EP2003/014867 (Glaxo Group Ltd) and PCT/EP2004/005494 (Glaxo Group Ltd).

Anticholinergic agents of interest are those compounds that act as antagonists at the muscarinic receptors, in particular those compounds which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva).

Antihistamines of interest (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine and cetirizine.

The invention thus provides, in a further aspect, a combination comprising Form 2 crystalline (Ia) monohydrochloride together with a PDE4 inhibitor. Preferably, the invention provides a combination comprising Form 2 crystalline (Ia) monohydrochloride together with a preferred PDE4 inhibitor as described hereinabove, e.g. cis-4-cyano-4-[3-(cyclopentyloxy)-4-methoxyphenyl]cyclohexane-1-carboxylic acid.

The invention thus provides, in a further aspect, a combination comprising Form 2 crystalline (Ia) monohydrochloride together with a corticosteroid. Preferably, the invention provides a combination comprising Form 2 crystalline (Ia) monohydrochloride together with a preferred corticosteroid as described hereinabove, e.g. fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

The invention thus provides, in a further aspect, a combination comprising Form 2 crystalline (Ia) monohydrochloride together with an anticholinergic. Preferably, the invention provides a combination comprising Form 2 crystalline (Ia) monohydrochloride together with a preferred anticholinergic as described hereinabove, e.g. ipratropium, oxitropium or tiotropium The invention thus provides, in a further aspect, a combination comprising Form 2 crystalline (Ia) monohydrochloride together with an antihistamine. Preferably, the invention provides a combination comprising Form 2 crystalline (Ia) monohydrochloride together with a preferred antihistamine as described hereinabove.

The invention thus provides, in a further aspect, a combination comprising Form 2 crystalline (Ia) monohydrochloride together with a PDE4 inhibitor and a corticosteroid. Preferably, the invention provides a combination comprising Form 2 crystalline (Ia) monohydrochloride together with a preferred antihistamine and a preferred corticosteroid as described hereinabove.

The invention thus provides, in a further aspect, a combination comprising Form 2 crystalline (Ia) monohydrochloride together with an anticholinergic and a PDE-4 inhibitor. Preferably, the invention provides a combination Form 2 crystalline (Ia) monohydrochloride together with a preferred PDE4 inhibitor and a preferred anticholinergic as described hereinabove.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

For a better understanding of the invention, the following Examples are given by way of illustration.

Analytical Methods

Figure 1:
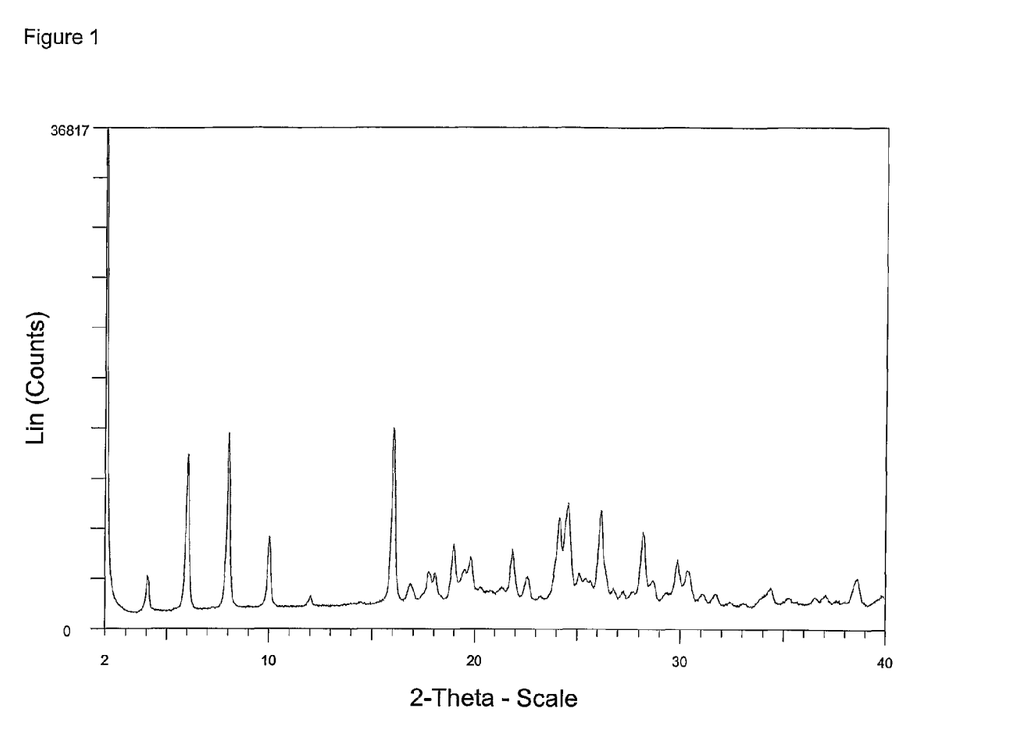
FIG. 1 shows an x-ray powder diffraction pattern of Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride) corresponding to Example 1(iv).

XRPD analysis shown in FIG. 1 was performed on a Bruker X-ray powder diffractometer, Model D8 Advance, serial number ROE 2357. The method runs from 2 to 40 degrees 2-Theta with a 0.0145 degree 2-Theta step size and a 1 second collection time at each step.

The X-ray powder diffraction (XRPD) analysis of Example 3 (shown in FIG. 2) was performed on a PANalytical X'Pert Pro powder diffractometer, model PW3040/60, serial number DY1850 using an X'Celerator detector. The acquisition conditions were: radiation: Cu Kα, generator tension: 40 kV, generator current 45 mA, start angle: 3.0° 2θ, step size 0.017° 2θ, time per step: 9205 seconds. The sample was prepared using a 0.5 mm external diameter glass capillary. Characteristic XRPD angles and d-spacings are recorded in Table 1.

The infrared absorption spectrum was recorded over the wavenumber range 4000 to 650 $cm^{-1}$ using a PerkinElmer Spectrum One FT-IR spectrometer equipped with a PerkinElmer Universal ATR (attenuated total reflection) sampling accessory.

1H NMR spectra were acquired on a 400 MHz Bruker DPX400 spectrometer at 300K. Sample was dissolved in $CDCl_3$ or dmso-d6 and chemical shifts were reported in ppm relative to the TMS signal at 0 ppm.

The differential scanning calorimetry analysis for Example 1(iv) was obtained with a Perkin Elmer instrument model Pyris 1. Samples were weighed into a 50 microlitre aluminium pan, an aluminium lid placed on top of the sample and compressed with a brass rod. An aluminium cover was placed on top of the pan and sealed using a universal press. An empty pan, lid and cover serving as a reference. Samples were equilibrated at 30° C. and heated at 10° C. per minute to a temperature of 300° C. The instrument was calibrated using indium, tin and lead standards.

Figure 3:
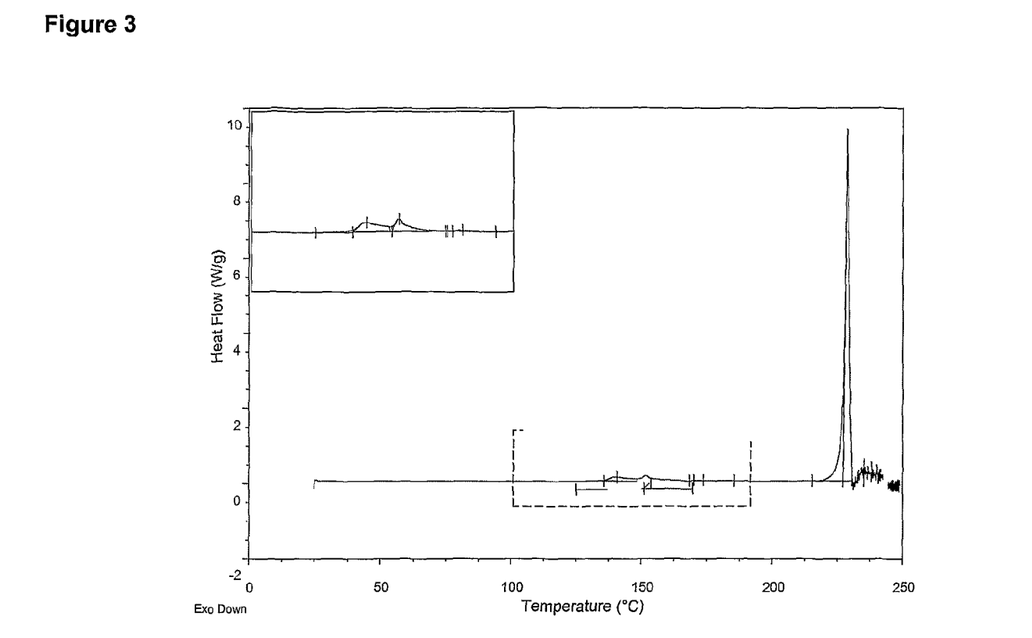
FIG. 3 shows a DSC trace for Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride, corresponding to Example 3. A series of minor endothermic events are seen above about 125° C. There are endotherms with onsets of 135.7° C. (event 1) 149.3° C. (event 2) and 170.3° C. (event 3). This is followed by a larger endotherm with an onset of 227.2° C.

The DSC trace of the product of Example 3 is shown in FIG. 3 and was obtained using a TA Instruments Q1000 calorimeter. The sample was weighed into an aluminium pan, a pan lid placed on top and lightly crimped without sealing the pan. The experiment was conducted using a heating rate of 10° C. $min^{-1}$.

Abbreviations

TBDMS-Cl: tert-butyldimethylsilyl chloride

DCM: dichloromethane

DMA: N,N-dimethylacetamide

MEK: 2-Butanone (methylethyl ketone)

NMP: N-methylpyrrolidone

IPA: Isopropylalcohol

IMS: industrial methylated spirit (in the following examples composition of IMS was Ethanol-96%, methanol 4%)

REFERENCE EXAMPLES

Preparation of Crystalline (Ia) Monohydrochloride as Per WO2004/106279)

a) Synthesis of 2-[4-((R)-2-hydroxy-2-phenylethylamino)phenyl]ethylamine (2)

To a 1000 mL 3-neck flask was added 10 g (74 mmol) of 2-(4-aminophenyl)ethylamine and 15 mL of 1,3-dimethyl-3,4,5,6-tetrahydro-2(1H)pyrimdinone (DMPU). The reaction flask was fitted with an overhead stirrer, a 125 mL addition funnel and a thermometer. The reaction flask was purged with nitrogen and placed in a cold water bath. The addition funnel was charged with 83 mL (83 mmol) of 1.0 M sodium bis(trimethylsilyl)amide in tetrahydrofuran. The sodium bis(trimethylsilyl)amide solution was added dropwise over 30 min with vigorous stirring. The addition funnel was removed and replaced with a rubber septum. (R)-styrene oxide (8.4 mL, 74 mmol) was added dropwise by syringe over 10 minutes. The rate of addition was controlled to maintain a temperature below 35° C. After 1 h, the reaction was quenched by dropwise addition of 88 mL water. The reaction mixture was transferred to a separatory funnel, diluted with 56 mL isopropyl acetate and washed with 84 mL saturated aqueous sodium chloride. The organic layer was washed a second time with a mixture of 84 mL water and 84 mL saturated aqueous sodium chloride and finally with 84 mL saturated aqueous sodium chloride. The organic layer was concentrated under vacuum. The residue was twice reconcentrated from isopropanol (55 mL portions) and then redissolved in isopropanol (235 mL) and heated to 70° C. with stirring. Concentrated hydrochloric acid (13.2 mL, 160 mmol) was added over two minutes. The mixture was allowed to cool to room temperature and stirred for 14 h. The precipitated product was isolated by filtration and washed with isopropanol and isopropyl acetate. The product was dried under vacuum for 3 h and then dissolved in 56 mL water and transferred to a separatory funnel. Isopropyl acetate (56 mL) and 10 N aqueous sodium hydroxide (19 mL, 190 mmol) were added. The separatory funnel was shaken and the phases separated. The organic layer was dried over sodium sulfate and concentrated to afford the product (2) as an orange-brown oil (11 g, 44 mmol, 59%). m/z: $[M+H^+]$ calcd for $C_{16}H_{20}N_2O$ 257.2. Found 257.2.

b) Synthesis of 2-bromo-(R)-1-tert-butyldimethylsiloxy-1-(3-formamido-4-benzyloxyphenyl)ethane (4)

(R)-2-Bromo-1-(3-formamido-4-benzyloxyphenyl)ethanol (intermediate 3) (9.9 g, 28 mmol) was dissolved in 36 mL dimethylformamide. Imidazole (2.3 g, 34 mmol) and t-butyldimethylsilylchloride (4.7 g, 31 mmol) were added. The solution was stirred under nitrogen atmosphere for 72 h. Additional imidazole (0.39 g, 5.7 mmol) and t-butyldimethylsilylchloride (0.64 g, 4.3 mmol) were added and the reaction was stirred for an additional 20 h. The reaction was diluted with a mixture of isopropyl acetate (53 mL) and hexanes (27 mL) and transferred to a separatory funnel. The organic layer was twice washed with a mixture of water (27 mL) and saturated aqueous sodium chloride (27 mL) followed by a final wash with saturated aqueous sodium chloride (27 mL). The organic layer was dried over sodium sulfate. Silica gel (23.6 g) and hexanes (27 mL) were added and the suspension was stirred for 10 minutes. The solids were removed by filtration and the filtrate concentrated under vacuum. The residue was crystallized from hexanes (45 mL) to afford 8.85 g (19 mmol, 68%) of intermediate 4 as a white solid. m/z: $[M+H^+]$ calcd for $C_{22}H_{30}NO_3SiBr$ 464.1, 466.1. Found 464.2, 466.4.

c) Synthesis of N-{2-[4((R)-2-hydroxy-2-phenylethylamino)phenyl]ethyl}(R)-2-tert-butyldimethylsiloxy-2-(3-formamido-4-benzyloxyphenyl)ethylamine (5)

Intermediate 4 (5.0 g, 11 mmol), intermediate 2 (3.5 g, 14 mmol), and dimethylsulfoxide (10 mL) were combined in a 100 mL round bottom flask and stirred to form a homogeneous solution. Potassium carbonate (6.0 g, 43 mmol) and sodium iodide (1.7 g, 11 mmol) were added and the reaction mixture was heated to 140° C. The reaction mixture was maintained at 140° C. for 10 min, then cooled to room temperature and diluted with water (24 mL) and isopropyl acetate (28 mL). The reaction was stirred until all solids dissolved and then transferred to a separatory funnel. The organic layer was washed with water (17 mL) followed by acetate buffer (5% v/v acetic acid, 12% w/v sodium acetate trihydrate in water, 18 ml) followed by sodium bicarbonate solution (5% w/v in water, 17 mL) followed by saturated aqueous sodium chloride (17 mL). The organic layer was dried over sodium sulfate and concentrated to afford intermediate 5 as a brown gelatinous solid (7.0 g, 11 mmol, >99%). m/z: $[M+H^+]$ calcd for $C_{38}H_{49}N_3O_4Si$ 640.4. Found 640.6.

d) Synthesis of N-{2-[4-((R)-2-hydroxy-2-phenylethylamino)phenyl]ethyl}-(R)-2-hydroxy-2-(3-formamido-4-benzyloxyphenyl)ethylamine (6)

Intermediate 5 (5.2 g, 8.1 mmol) was dissolved in tetrahydrofuran (26 mL) and triethylamine trihydrofluoride (1.4 mL, 8.6 mmol) was added. The solution was stirred for 20 h. The reaction was quenched by addition of water (7.6 mL) followed by 10.0 N sodium hydroxide (3.8 mL, 38 mmol). After 3 min, the reaction was diluted with isopropyl acetate (20 mL) and transferred to a separatory funnel. The mixture was shaken and the biphasic mixture was filtered through celite to remove undissolved solids. The filtrate was returned to a separatory funnel and the phases were separated. The organic layer was washed with a mixture of 9 mL water and 9 mL saturated aqueous sodium chloride followed by 15 mL of saturated aqueous sodium chloride. The organic layer was dried over sodium sulfate and concentrated to afford the product 6 as a brown gelatinous solid (4.2 g, 8.0 mmol, 99%). m/z: [M+H$^+$] calcd for $C_{32}H_{35}N_3O_4$ 526.3. Found 526.4.

e) Synthesis of N-{2-[4-((R)-2-hydroxy-2-phenyl-ethylamino)phenyl]ethyl}-(R)-2-hydroxy-2-(3-formamido-4-hydroxyphenyl)ethylamine (1)

Intermediate 6 (2.5 g, 4.8 mmol) was dissolved in 8.0 mL of ethanol and treated with activated charcoal, Darco G-60 (1.25 g). The suspension was stirred at 50° C. for 20 min and then filtered to remove the Darco. To the filtrate was added 10% palladium on activated carbon (250 mg) and the suspension placed on a Parr shaker. The reaction was shaken for 10 h under 30 psi hydrogen gas. The reaction was filtered through celite and concentrated under vacuum to afford compound 1 as a brown gelatinous solid (1.9 g, 4.3 mmol, 91%). $^1$HNMR (300 MHz, DMSO-$d_6$) δ 2.40-2.68 (m, 6H), 2.92-3.18 (m, 2H), 4.35-4.45 (m, 1H), 4.60-4.69 (m, 1H), 5.22-5.30 (m, 1H), 6.82 (s, 1H), 6.85 (s, 1H), 6.68-6.86 (m, 4H), 7.12-7.36 (m, 5H), 7.95 (d, 1H, J=1.4 Hz), 8.19 (s, 1H), 9.49 (br s, 1H). m/z: [M+H$^+$] calcd for $C_{25}H_{29}N_3O_4$ 436.2. Found 436.4.

f) Crystallization of N-{2-[4-((R)-2-hydroxy-2-phenylethylamino)phenyl]ethyl}-(R)-2-hydroxy-2-(3-formamido-4-hydroxyphenyl)ethylamine monohydrochloride In a 500 mL round bottom flask, compound 1 (5.2 g, 11.9 mmol) was dissolved in 187.9 mL isopropyl alcohol with stirring at 40° C. Complete dissolution was achieved within 10 minutes. The flask was then charged with a solution containing 1.0 N HCl (11.3 mL, 11.3 mmol, 0.95 eq.) and $H_2O$ (29.6 mL). The solution was stirred and the product crystallized over several hours. After 6 h, the crystals were isolated by filtration and washed with 15 mL ice-cold 15% water in isopropyl alcohol solution followed by 15 mL of isopropyl alcohol. The crystals were dried under house vacuum for 12-16 h to afford the monohydrochloride salt of compound 1 (3.92 g, 8.3 mmol, 70% yield, 98.89% purity by HPLC) as a white crystalline solid. Water content 0.2%, $^1$H NMR (300 MHz, DMSO-$d_6$): δ (ppm) 10.13 (s, 1H), 9.62 (m, 1H), 8.93 (br s, 1H), 8.66 (br s, 1H), 8.27 (d, 1H, J=1.92), 8.13 (d, 1H, J=1.65), 7.21-7.40 (m, 5H), 6.86-6.94 (m, 4H), 6.57 (d, 2H, J=8.52), 6.05 (d, 1H, J=3.57), 5.45-5.55 (m, 2H), 4.80 (m, 1H), 4.70 (m, 1H), 2.70-3.24 (m, 8H). Elemental analysis (wt %) calcd for $C_{25}H_{29}N_3O_4$·HCl: C, 63.62; H, 6.41; N, 8.90; Cl, 7.51. found: C, 63.47; H, 6.54; N, 8.81; Cl, 7.78.

Example 1 i) 2-Bromo-(R)-1-tert-butyldimethylsiloxy-1-(3-formamido-4-benzyloxyphenyl)ethane A solution of TBDMS-Cl (40.1 g, 0.26 mol) in DCM (37.5 mL) was added to a slurry of imidazole (21.86 g, 0.32 mol) and (R)-2-bromo-1-(3-formamido-4-benzyloxyphenyl)ethanol (74.54 g, 0.21 mol) in DCM (260 mL) over 8 minutes. The mixture was stirred for 22 hours. The reaction was quenched with water (190 mL) and the aqueous layer was extracted with DCM (37.5 mL). The combined DCM layers were distilled at atmospheric pressure to a volume of ca. 110 mL. On cooling, spontaneous crystallisation occurred. Isooctane (750 mL) was added dropwise over 20 minutes. The slurry was cooled to 0° C. and the solids were collected by filtration then washed with 9:1 v/v isooctane:DCM (3×75 mL) and dried in vacuo to give the title compound as a colourless solid (89.65 g, 90% th). $^1$H NMR in accord with structure (400 MHz, CDCl$_3$) δ(ppm): −0.06 (3H) s; 0.11 (3H) s; *0.12 (3H) s; *0.89 (9H) s; 0.90 (9H) s; *3.38-3.49 (2H) m; 4.78-4.87 (1H) m; *5.09 (2H) s; 5.10 (2H) s; 6.96 (1H) d, J=8.6 Hz; *7.06 (1H) d of d, J=8.3, 2.0 Hz; 7.11 (1H) d of d, J=8.3 Hz, 2.0 Hz; 7.25-7.27 (1H) m; 7.36-7.45 (5H) m; *7.70 (1H) d, J=11.0 Hz; 7.79 (1H) s; 8.38 (1H) d, J=2.0 Hz; 8.42 (1H) d, J=1.5 Hz; *8.76 (1H) d, J=11.8 Hz.

*Peaks are due to ca 25M % of the minor rotamer.

ii) N-{2-[4-((R)-2-hydroxy-2-phenylethylamino)phenyl]ethyl}-(R)-2-hydroxy-2-(3-formamido-4-benzyloxyphenyl)ethylamine monohydrochloride 2-[4-((R)-2-Hydroxy-2-phenylethylamino) phenyl]ethylamine (19.8 g, 60 mmol) was dissolved in water (80 mL). Isopropyl acetate (100 mL) was added with stirring. 32% w/v aqueous sodium hydroxide solution (17.2 mL) was added with stirring over 8 minutes. The organic layer was washed with water (100 mL) then distilled at atmospheric pressure to a volume of ca. 70 mL.

To this solution was added DMA (50 mL) followed by 2-bromo-(R)-1-tert-butyldimethylsiloxy-1-(3-formamido-4-benzyloxyphenyl)ethane (20 g, 43 mmol) and potassium carbonate (7.44 g, 54 mmol). The mixture was heated at 90° C. (oil bath temperature) for 17 hours then cooled to 50° C. Water (150 mL) was added and the mixture was cooled further to room temperature. MEK (150 mL) was added and the layers were separated. The organic layer was washed with 17:40:340 v/w/v acetic acid:sodium acetate:water (100 mL) followed by 29% w/v aqueous sodium chloride solution (100 mL). The organic layer was diluted with MEK (50 mL) and then distilled at atmospheric pressure to a volume of ca 150 mL, followed by addition of more MEK (50 mL). The mixture was heated to 37° C. and a solution of cesium fluoride (8.1 g, 51.6 mmol) in methanol (100 mL) was added. Heating at 37° C. was continued for 7.5 hours then the mixture was cooled to 30° C. The reaction was quenched with 44% w/v aqueous potassium carbonate solution (100 mL) and water (20 mL) was added. The organic layer was washed with 29% w/v aqueous sodium chloride solution (100 mL) then treated with acetic acid (3.7 mL, 64.6 mmol). The mixture was washed with 29% w/v aqueous sodium chloride solution (100 mL) followed by 6% w/v aqueous sodium chloride solution (3×100 mL).

The solution was diluted with MEK (100 mL) then distilled to a volume of ca 120 mL. MEK (80 mL) was added and the mixture was seeded$^+$ with title compound. The mixture was distilled again to a volume of ca. 140 mL. More MEK (60 mL) was added and the mixture was cooled to room temperature. The solids were collected by filtration, washed with MEK (3×20 mL) and dried in vacuo to give the title compound as a colourless solid (18.64 g, 77% th). $^1$H NMR in accord of structure (400 MHz, DMSO-$d_6$) δ(ppm): 2.70-2.89 (2H) m; 2.95 (1H) m; 3.01-3.14 (4H) m; 3.14-3.23 (1H) m; 4.71 (1H) m; 4.81 (1H) m; *5.17 (1H) s; 5.23 (1H) s; 5.46 (1H) d, J=4.4

Hz; 5.50 (1H) m; 6.10 (1H) d, J=3.2 Hz; 6.59 (2H) d, J=8.3 Hz; 6.94 (2H) d, J=8.3 Hz; 7.03 (1H) d of d, J=8.6, 2.0 Hz; 7.12 (1H) d, J=8.6 Hz; 7.25 (1H) m; 7.30-7.36 (3H) m; 7.36-7.42 (4H) m; 7.50 (2H) d, J=7.3 Hz; 8.26 (1H) d, J=2.0 Hz; 8.35 (1H) d, J=1.7 Hz; *8.54 (1H) d, J=11.0 Hz; 8.63 (2H) broad res; *9.64 (1H) m; 9.67 (1H) s.

\* Peaks are due to ca 11.5M % of the minor rotamer.
⁺ seeds may be obtained using the methods described hereinabove iii) N-{2-[4-((R)-2-Hydroxy-2-phenylethylamino) phenyl]ethyl}-(R)-2-hydroxy-2-(3-formamido-4-hydroxyphenyl)ethylamine monohydrochloride A mixture of N-{2-[4-((R)-2-hydroxy-2-phenylethylamino)phenyl]ethyl}-(R)-2-hydroxy-2-(3-formamido-4-benzyloxyphenyl)ethylamine monohydrochloride (40 g) and 5% Pd/C catalyst (Englehard 167, 50% wet with water) (200 mg) in NMP (120 ml) was stirred under hydrogen at 22±2° C. The mixture was filtered (Whatman GF/F filter) when analysis, by hplc (detection at 220 nm), of the reaction mixture showed <0.5% (by area) of the starting material (product of Ex 1ii). The filter cake was washed with a mixture of NMP and IPA (1:1) (80 ml).

The combined filtrates were stirred and heated to 69±3° C. Water (10 ml) was added. IPA (100 ml) was added at a rate that maintained the temperature at 69±3° C. Seed crystals (0.8 g) were added. IPA (50 ml) was added over 15 minutes. The resulting mixture was stirred for about 0.75 h. IPA (250 ml) was then added over about 2.5 h. The resulting slurry was allowed to cool slowly to 20±3° C. and stirred at this temperature for ca 16 h.

The resulting slurry was cooled to 3±3° C. and stirred at this temperature for 4 h. The slurry was filtered and the collected solid was washed successively with IPA/water (10:1) (80 ml) and IPA (160 ml). The solid was dried under vacuum at ca 50° C. to give the title compound as a white solid (29.7 g).

Yield: 88% th, 74% w/w

NMR: (400 MHz, DMSO-d₆) δ(ppm): 2.73-2.89 (2H) m; 2.95 (1H) m; 3.01-3.14 (4H) m; 3.15-3.24 (1H) m; 4.72 (1H) m; 4.82 (1H) m; 5.46 (1H) d, J=4.7 Hz; 5.48 (1H) m; 6.03 (1H) d, J=3.4 Hz; 6.59 (2H) d, J=8.6 Hz; 6.89 (1H) d, J=8.1 Hz; 6.91-6.98 (3H) m; *7.01 (1H) d, J=8.6 Hz; *7.14 (1H) s; 7.25 (1H) t, J=7.3 Hz; 7.33 (2H) t, J=7.3, 7.6 Hz; 7.39 (2H) d, J=7.6 Hz; 8.13 (1H) d, J=1.5 Hz; 8.29 (1H) d, J=1.7 Hz; *8.53 (1H) d, J=11.0 Hz; 8.57-9.08 (2H) broad res; *9.36 (1H) d, J=11.0 Hz; 9.60 (1H) s; *9.92 (1H) s; 10.10 (1H) s.

\* Peaks are due to ca 11 M % of the minor rotamer.

iv) Recrystallisation of N-{2-[4-((R)-2-Hydroxy-2-phenylethylamino)phenyl]ethyl}-(R)-2-hydroxy-2-(3-formamido-4-hydroxyphenyl)ethylamine monohydrochloride The title monohydrochloride (5 g) was suspended in aqueous industrial methylated spirit (IMS) (2:1 IMS:water, 72.5 ml) in a 100 ml round bottomed flask. The mixture was warmed to 78° C. to give a clear solution. This was filtered, washed through with aqueous IMS (2:1 IMS:water, 2.5 ml) and the liquor rewarmed to 78° C. to re-dissolve the solid that precipitated during the filtration. The temperature was adjusted to 65° C. and seeded with monohydrochloride (10 mg). The mixture was held at 60-65° C. for 2 hours and then cooled to 20-25° C. and stirred at that temperature for 14 hours. The suspension was chilled to 0-5° C. and held at that temperature for 3 hours. The product was collected via filtration, and washed with aqueous IMS (2:1 IMS: water, 2×7.5 ml) and then IMS (3×7.5 ml) to give the title compound as a white solid, which was dried at 50° C. under vacuum overnight (60.28 g).

Expected yield: 80% th, 80% w/w

The XRPD pattern of this product is shown in FIG. 1.

The differential scanning calorimetry trace for this product shows an absence of discernable endothermic features below about 125° C., with minor endothermic events having onsets at about 133° C., about 151° C. and at about 170° C.

Example 2

Alternative preparation of N-{2-[4-((R)-2-hydroxy-2-phenylethylamino)phenyl]ethyl}-(R)-2-hydroxy-2-(3-formamido-4-benzyloxyphenyl)ethylamine monohydrochloride 2-Bromo-(R)-1-tert-butyldimethylsiloxy-1-(3-formamido-4-benzyloxphenyl)ethane (100 g, 215 mmol), 2-[4-((R)-2-Hydroxy-2-phenylethylamino)phenyl]ethylamine bis-hydrobromide salt (99 g, 237 mmol) and potassium carbonate (119 g, 861 mmol) were charged to a reactor. NMP (500 mL) was added and the mixture was heated at 110-115° C. for 5 hours then cooled to 50° C. Water (900 mL) was added followed by 1-pentanol (500 mL) and the mixture was cooled further to room temperature (≦35° C.) when the layers were separated. The organic layer was washed with water (500 mL) followed by 2% w/v aqueous sodium chloride solution (500 mL).

To the organic layer was added acetic acid (20 mL, 350 mmol) followed by a solution of cesium fluoride (39 g, 257 mmol) in methanol (500 mL). The mixture was heated at 55° C. for 4 hours. The reaction was quenched with 37% w/v aqueous potassium carbonate solution (500 mL) then cooled to 30° C. (≦35° C.). The organic layer was washed with 10% w/v aqueous sodium chloride solution (500 mL) then treated with acetic acid (18.5 mL, 324 mmol). The mixture was washed with 10% w/v aqueous sodium chloride solution (2×500 mL).

The solution was diluted with 1-pentanol (1 L), seeded with title compound 0.2 g) and aged for 30 minutes. The mixture was distilled under vacuum to a volume of ca. 1.4 L and the mixture was cooled to room temperature. The solids were collected by filtration, washed with 1-pentanol (2×300 mL) followed by ethyl acetate (300 mL) and dried in vacuo to give the title compound as a colourless solid (86.09 g, 71% th). ¹H NMR in accord of structure (400 MHz, DMSO-d₆) δ(ppm): 2.70-2.89 (2H) m; 2.95 (1H) m; 3.01-3.14 (4H) m; 3.14-3.23 (1H) m; 4.71 (1H) m; 4.81 (1H) m; *5.17 (1H) s; 5.23 (1H) s; 5.46 (1H) d, J=4.4 Hz; 5.50 (1H) m; 6.10 (1H) d, J=3.2 Hz; 6.59 (2H) d, J=8.3 Hz; 6.94 (2H) d, J=8.3 Hz; 7.03 (1H) d of d, J=8.6, 2.0 Hz; 7.12 (1H) d, J=8.6 Hz; 7.25 (1H) m; 7.30-7.36 (3H) m; 7.36-7.42 (4H) m; 7.50 (2H) d, J=7.3 Hz; 8.26 (1H) d, J=2.0 Hz; 8.35 (1H) d, J=1.7 Hz; *8.54 (1H) d, J=11.0 Hz; 8.63 (2H) broad res; *9.64 (1H) m; 9.67 (1H) s.

• Peaks are due to ca 11.5M % of the minor rotamer.

Example 3

Recrystallisation of N-{2-[4-((R)-2-Hydroxy-2-phenylethylamino)phenyl]ethyl}-(R)-2-hydroxy-2-(3-formamido-4-hydroxyphenyl)ethylamine monohydrochloride The title monohydrochloride (30 g) was suspended in aqueous methanol (2:1 methanol:water, 600 ml) in a 1 L reactor. The mixture was warmed to 64° C. to give a clear solution. This was filtered and the liquor re-warmed to re-dissolve the solid that precipitated during the filtration. The temperature was adjusted to 56° C. and seeded with title compound[+] (0.6 g). The mixture was held at 56° C. for 30 minutes and then cooled to 20° C. over 2 hours. The suspension was heated to 50° C. over one hour and held at 50° C. for 1 hour. The mixture was cooled to 20° C. over 2.5 hours. The suspension was heated to 50° C. over one hour and held at 50° C. for 1 hour. The mixture was cooled to 10° C. over 2.5 hours and held at 10° C. for 8 hours. The product was collected via filtration, and washed with aqueous methanol (2:1 methanol: water, 60 ml) and then methanol (60 ml) to give the title compound as a white solid, which was dried at 40° C. under vacuum overnight.

Yield: 76% th

Figure 2:
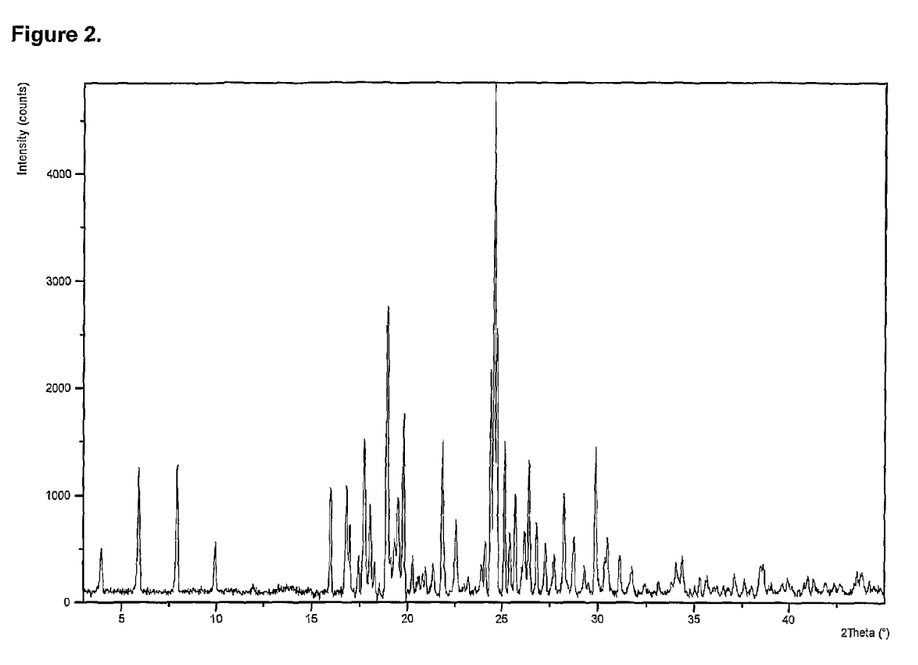
FIG. 2 shows an x-ray powder diffraction pattern of Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride corresponding to Example 3.

IR (measured as described hereinabove) gave significant absorption bands at about 663, 698, 747, 764, 788, 809, 827, 875, 969, 995, 1024, 1056, 1081, 1101, 1212, 1294, 1371, 1440, 1520, 1543, 1596, 1659, 3371 and 3552 cm$^{-1}$ The X-ray powder diffraction (XRPD) analysis of the product is shown in FIG. 2. Characteristic XRPD angles and d-spacings are recorded in Table 1.

[+] seeds may be obtained using the methods described hereinabove

TABLE 1

Characteristic XRPD peak angles and d-spacings

| Two Theta (deg)* | d-spacing (Å) |
|---|---|
| 4.0 | 22.3 |
| 6.0 | 14.8 |
| 8.0 | 11.1 |
| 10.0 | 8.9 |
| 12.0 | 7.4 |
| 16.0 | 5.5 |
| 16.8 | 5.3 |
| 17.0 | 5.2 |
| 17.4 | 5.1 |
| 17.7 | 5.0 |
| 18.1 | 4.9 |
| 18.3 | 4.8 |
| 19.0 | 4.7 |
| 19.3 | 4.6 |
| 19.5 | 4.5 |
| 19.8 | 4.5 |
| 20.3 | 4.4 |
| 20.6 | 4.3 |
| 21.0 | 4.2 |
| 21.4 | 4.2 |
| 21.9 | 4.1 |
| 22.6 | 3.9 |
| 23.9 | 3.7 |
| 24.1 | 3.7 |
| 24.4 | 3.6 |
| 24.6 | 3.6 |
| 24.7 | 3.6 |
| 25.1 | 3.5 |
| 25.4 | 3.5 |
| 25.7 | 3.5 |
| 26.2 | 3.4 |
| 26.4 | 3.4 |
| 26.8 | 3.3 |
| 28.2 | 3.2 |
| 29.9 | 3.0 |

*For copper Kα radiation.

The invention claimed is:

1. A process for preparing a monohydrochloride salt of compound (I)

(I)

wherein *C and **C denote asymmetric carbon atoms, which process comprises the steps of:
a) contacting a compound of formula (II):

(II)

wherein $P^1$ represents a hydroxyl protecting group, and $P^2$ and $P^3$ each independently represents hydrogen or a protecting group;
with a weak acid, to effect selective protonation;
b) contacting the product of (a) with a source of chloride ions, to effect anion exchange;
c) deprotecting to remove $P^1$, and where necessary $P^2$ and $P^3$;
d) isolating compound (I) as the monohydrochloride; and optionally
e) crystallizing or recrystallizing compound (I).

2. A process according to claim 1, wherein the compound of formula (I) is the compound (Ia):

(Ia)

and the compound of formula (II) is the compound (IIa)

(IIa)

wherein $P^1$ is as defined in claim 1.

3. A process according to claim 1 wherein the weak acid is acetic acid.

4. A process according to claim 1 wherein the group $P^1$ represents benzyl.

5. A process according to claim 1 wherein the source of chloride ions is sodium chloride.

6. Crystalline monohydrochloride salt of the compound of formula (Ia) prepared by a process according to claim 1.

7. Crystalline (Ia) monohydrochloride according to claim 6 wherein the product of said process is characterised by an x-ray powder diffraction pattern in which the peak positions are substantially in accordance with the peak positions of the pattern shown in FIG. 1.

8. Crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia)) monohydrochloride which is characterised by a differential scanning calorimetry trace which shows an absence of discernable endothermic features below about 125° C.

9. Crystalline Compound (Ia) monohydrochloride according to claim 8 which is characterised by a differential scanning calorimetry trace which shows an absence of discernable endothermic features below about 125° C. and an onset of significant endothermic heat flow at about 229° C.

10. Crystalline Compound (Ia) monohydrochloride according to claim 8 which is characterised by a differential scanning calorimetry trace which shows an absence of discernable endothermic features below about 125° C., two or more minor endothermic events between about 130° C. and about 180° C. and an onset of significant endothermic heat flow at about 229° C.

11. Crystalline Compound (Ia) monohydrochloride according to claim 10 wherein said minor endothermic events occur at about 133° C., at about 151° C. and at about 170° C.

12. Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia)) monohydrochloride in substantially pure form.

13. A process for obtaining Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia)) monohydrochloride in substantially pure form which process comprises:
   Ba) forming a mixture of N-{2-[4-((R)-2-hydroxy-2-phenylethylamino)phenyl]ethyl}-(R)-2-hydroxy-2-(3-formamido-4-hydroxyphenyl)ethylamine monohydrochloride in an aqueous organic solvent, by contacting said monohydrochloride with said solvent and heating in a range from about 60° C. to about 70° C.;
   Bb) adjusting the temperature of said mixture in the range from about 52° C. to about 58° C.;
   Bc) seeding said mixture with Form 2 crystals;
   Bd) cooling said mixture to a temperature in the range from about 15° C. to 25° C.;
   Be) heating said mixture to a temperature in the range from about 47° C. to about 52° C.;
   Bf) repeating steps Bd) and Be) to obtain the desired Form 2.

14. A method for the treatment of a clinical condition in a mammal for which a selective adrenoreceptor agonist is indicated, wherein the condition is asthma or chronic obstructive pulmonary disease (COPD), the method comprising administering a therapeutically effective amount of Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride.

15. A pharmaceutical formulation comprising Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride and a pharmaceutically acceptable carrier or excipient, and optionally one or more other therapeutic ingredients.

16. A combination comprising Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride and one or more other therapeutic ingredients.

17. A combination according to claim 16 wherein the other therapeutic ingredient is a PDE4 inhibitor or an anticholinergic or a corticosteroid.

18. A combination according to claim 16 comprising Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride and 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

19. A combination according to claim 16 comprising Form 2 crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride (Compound (Ia) monohydrochloride and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

20. A process according to claim 13, wherein said Ba) step comprises heating the mixture to a temperature of about 65° C.

21. A process according to claim 13, wherein said Bb) step comprises adjusting the temperature of said mixture from about 52° C. to about 55° C.

22. A method according to claim 14, wherein the mammal is a human.

23. A method according to claim 14, wherein the clinical condition is asthma.

24. A method according to claim 14, wherein the clinical condition is COPD.

* * * * *